(12) United States Patent
Oesterlein et al.

(10) Patent No.: US 10,888,237 B2
(45) Date of Patent: Jan. 12, 2021

(54) METHOD AND SYSTEM FOR DETERMINING VENTRICULAR FAR FIELD CONTRIBUTION IN ATRIAL ELECTROGRAMS

(71) Applicant: Karlsruhe Institute of Technology, Karlsruhe (DE)

(72) Inventors: Tobias Oesterlein, Karlsruhe (DE); Olaf Dössel, Bruchsal (DE); Daniel Frisch, Karlsruhe (DE); Axel Loewe, Karlsruhe (DE); Gustavo Lenis, Aachen (DE); Nicolas Pilia, Germersheim (DE)

(73) Assignee: Karlsruhe Institute of Technology, Karlsruhe (DE)

( * ) Notice: Subject to any disclaimer, the term of this patent is extended or adjusted under 35 U.S.C. 154(b) by 178 days.

(21) Appl. No.: 16/111,092

(22) Filed: Aug. 23, 2018

(65) Prior Publication Data
US 2019/0059765 A1 Feb. 28, 2019

(30) Foreign Application Priority Data
Aug. 24, 2017 (EP) .................................... 17187850

(51) Int. Cl.
*A61B 5/04* (2006.01)
*A61B 5/0456* (2006.01)
(Continued)

(52) U.S. Cl.
CPC ........ *A61B 5/04012* (2013.01); *A61B 5/0075* (2013.01); *A61B 5/0422* (2013.01);
(Continued)

(58) Field of Classification Search
CPC . A61B 5/0075; A61B 5/04012; A61B 5/0422; A61B 5/0452; A61B 5/0456;
(Continued)

(56) References Cited

U.S. PATENT DOCUMENTS

2018/0279896 A1* 10/2018 Ruppersberg ...... A61B 5/04028

FOREIGN PATENT DOCUMENTS

WO WO 2017/041890 * 3/2017 ............. A61B 5/042

OTHER PUBLICATIONS

Oesterlein, Tobias Georg, et al. "Removing ventricular far-field signals in intracardiac electrograms during stable atrial tachycardia using the periodic component analysis." Journal of electrocardiology 48.2 (2015): 171-180. https://doi.org/10.1016/j.jelectrocard.2014.12.004 (Year: 2015).*

(Continued)

*Primary Examiner* — Jonathan T Kuo
(74) *Attorney, Agent, or Firm* — Brake Hughes Bellermann LLP

(57) ABSTRACT

A computer system for determining Ventricular Far Field contribution in atrial electrograms of a patient. The system includes an interface module configured to receive a plurality of electrical signals generated by a plurality of sensors wherein the plurality of electrical signals relate to a plurality of locations in an atrium of the patient; a reference module configured to determine a reference signal reflecting electrical excitation of the patient's ventricles; and a data processing module. The data processing module is configured to select from the plurality of the received electrical signals such electrical signals which are recorded a number of conditions. The data processing module is further configured to determine a spatio-temporal distribution of the Ventricular Far Field inside the atrium by approximating the spatio-temporal distribution (VFFc) based on signal data of the selected signals by using an approximation model.

21 Claims, 13 Drawing Sheets

(51) Int. Cl.
    *A61B 5/042*     (2006.01)
    *A61B 5/00*     (2006.01)
    *A61B 5/1455*     (2006.01)
    *A61B 5/0452*     (2006.01)

(52) U.S. Cl.
    CPC .......... *A61B 5/0452* (2013.01); *A61B 5/0456* (2013.01); *A61B 5/14551* (2013.01)

(58) Field of Classification Search
    CPC ........ A61B 5/14551; A61B 5/02–0295; A61B 5/0402–0472
    See application file for complete search history.

(56) References Cited

OTHER PUBLICATIONS

Frisch, Daniel, et al. "Mapping and Removing the Ventricular Far Field Component in Unipolar Atrial Electrograms." IEEE Transactions on Biomedical Engineering (2020). DOI: 10.1109/TBME.2020.2973471 (Year: 2020).*

H. Nakagawa et al.: "Rapid high resolution electroanatomical mapping: evaluation of a new system in a canine atrial linear lesion model," Circulation. Arrhythmia and Electrophysiology, 5(2): 417-424, 2012.

U. Tedrow et al.: "Recording and Interpreting Unipolar Electrograms to Guide Catheter Ablation," Heart Rhythm, vol. 8, Issue 5, pp. 791-796, 2011.

* cited by examiner

METHOD AND SYSTEM FOR DETERMINING VENTRICULAR FAR FIELD CONTRIBUTION IN ATRIAL ELECTROGRAMS

CROSS REFERENCE TO RELATED APPLICATION

This application claims priority to, and is a continuation of EP Application No. EP17187850, filed on Aug. 24, 2017, entitled "Method and System for Determining Ventricular Far Field Contribution in Atrial Electrograms," the entirety of which is hereby incorporated by reference.

TECHNICAL FIELD

The present disclosure generally relates to electronic data processing of clinical measurement data, and more particularly, relates to methods, computer program products and systems for determining Ventricular Far Field (VFF) contribution in atrial electrograms based on clinical sensor data.

BACKGROUND

For the diagnosis of a patient's cardiac arrhythmias medical heart specialists record the electrical activity of the patient's heart with catheters having sensors (electrodes) to measure the electrical potential inside the heart. The resulting sensor signal is called an electrogram. Such electrograms as well as the location (position) of the respective sensors during the measurement can be recorded by using electro-anatomical mapping systems (EAMS). The analysis of electrograms can be used to support a medically trained person in the diagnosis of potential heart diseases and for taking appropriate therapeutic measures.

The contraction of the heart is triggered by an electrical pulse which is running in the form of a depolarization wave over the heart muscle and generates an electrical field in its environment. The field strength decreases with the distance r. While atrial tissue typically has a thickness of just a few millimeters, ventricular tissue typically has a thickness of more than a centimeter. For this reason, the electrical field generated in the ventricles of the heart is also measurable in the atria where it is called the Ventricular Far Field (VFF). Further, the VFF can also be measured on the body surface of the patient, leading to an electrocardiogram (ECG) potential.

Measurement technology can be used to measure the electrical potential in relation to a reference potential. Inside the human body there is no absolute and constant reference potential available. Therefore, in clinical measurements, an artificial reference potential can be generated. For example, this can be achieved by averaging the electrical potentials of the patient's right arm, left arm and left leg, thus providing the reference signal Wilson Central Terminal (WCT). The electrodes (e.g., sensors) in the inner of the heart measure the potential in relation to this virtual "zero" potential as a unipolar electrogram.

In unipolar electrograms primarily the information about the excitation of heart areas in close proximity to the catheter is useful for diagnostic purpose. For example, for diagnosis of atrial flutter the propagation of the electrical excitation in the patient's atria is analyzed. The respective signals reflect the atrial activity in respective electrograms. However, such electrograms are typically superimposed by noise signals which make the diagnostic analysis of the data more difficult.

Prior art approaches typically subtract the signals of two neighboring electrodes to eliminate disturbing noise. However, the resulting bipolar electrogram cannot be accurately assigned to a physical location in the patient's heart anymore resulting in a spatial inaccuracy. Further, it is not possible to precisely derive the local atrial excitation from the morphology from the bipolar electrograms because its shape and amplitude significantly depend on the angle between the measurement electrode and the direction of the excitation wave. Therefore, diagnostic indicators depending on shape or amplitude can produce misleading results.

Other prior art approaches observe recorded electrograms over longer time intervals (e.g., greater than 5 seconds) to learn the VFF component and then try to separate the VFF components from the atrial activity components by using statistical methods. Multiple statistical methods (e.g., Principal Component Analysis (PCA), Template Matching and Subtraction (TMS) or Periodic Component Analysis (PiCA)) may be used. However, the temporal coupling between ventricles and atria is critical with regards to the selection of the appropriate method. If this is not recognized in a correct manner, the method may produce errors.

SUMMARY

Therefore, there is a need to provide an improved method for determining the VFF component in electrograms with improved accuracy without additional risks for the patient. This technical problem is solved by the features of a computer system, a computer-implemented method and a computer program product as disclosed herein. Once the VFF component is determined, it can be removed from the electrograms which allows an accurate interpretation of the sensor data leading to improved diagnostics.

In some embodiments, a computer system is provided for determining Ventricular Far Field contribution in atrial electrograms of a patient. The computer system includes an interface module to receive a plurality of electrical signals generated by a plurality of sensors. The sensors may be the electrodes of a catheter. The plurality of electrical signals relate to a plurality of locations in an atrium of the patient. In other words, the electrodes of the catheter record the signal at different locations within the atrium while the catheter is moved by a medically trained person. The respective signal data is received by the interface module.

The system further includes a reference module to determine a reference signal reflecting electrical excitation of the patient's ventricles. For example, in one embodiment, receiving the reference signal may originate from one or more electrocardiogram sensors measuring at least the R wave of the patient's ventricular electrical activity. In some embodiments, the reference signal may be received from a coronary sinus catheter sensor. In some embodiments the reference signal may be computed by blind source separation or analysis of periodicity from the electrical signal data recorded by the plurality of sensors (electrodes). In some embodiments, the reference signal may be determined from information about the ventricular contraction obtained by using optical techniques including laser interferometry, pulse oximetry and/or near-infrared spectroscopy.

Further, the computer system includes a data processing module configured to select from the plurality of the received electrical signals such electrical signals which are recorded under one or more of the following conditions (the respective signals are recorded at locations inside the atrium where the respective sensor has no contact to the atrial tissue, the respective signals are recorded, irrespective of the sensor location, during time intervals where the respective (adjacent) part of the atrium shows no electrical activity, and/or the respective signals are recorded, irrespective of the sensor location, during time intervals which comprise a plurality of heart beat intervals and are subject to subsequent spatial smoothing.

In other words, signals which are suitable for determining the VFF contribution in the atrium are such signals that were either recorded while the catheter electrodes were entirely surrounded by blood (no atrial tissue contact) or, even in case of atrial tissue contact, were recorded when the atrium showed no activity. Of course, also signals recorded while no atrial tissue contact occurred and no atrial activity occurred are suitable signals for the further analysis. In some embodiments, sensor signals may be recorded at a particular region over a longer period which includes multiple heart beat intervals. In this case, subsequent spatial smoothing of such signals can be used to eliminate the disturbing influence of atrial activity even if the signals were recorded at locations where the sensor had contact to the atrial tissue or was located close enough to the atrial tissue so that atrial activity still had an impact of the sensor signals.

The data processing module further determines a spatio-temporal distribution of the VFF inside the atrium by approximating the spatio-temporal distribution based on signal data of the selected signals by using an approximation model. Different approximation models can be used. For example, a linear spatial model, a non-linear spatial model, a temporal model, and/or a look-up table may be used. Approximating can be implemented in different ways. In some embodiments, polynomial approximation may be used. In some embodiments, approximation with a dipole source model may be used. In some embodiments, the approximation is performed with spatio-temporal linear combination of the recorded signal data. In some embodiments, the approximation is performed with Radial Basis Functions. In some embodiments, the approximation is performed with using Look-Up Tables, which contain the recorded signal data of the VFF component at the respective measurement position. In some embodiments, the approximation is performed by transforming the signal data to a regular grid before providing it in form of a Look-Up Table. In some embodiments, spatio-temporal smoothing may be applied to the signal data to smoothen the recorded data.

The spatio-temporal distribution represents the VFF contribution at each respective measuring location of the sensors recording the sensor data for the respective electrograms. In other words, for each electrogram which represents the measurement signal data at a particular location at a particular point in time within the patient's atrium the contribution of the VFF at this location can be derived from the spatio-temporal distribution. Any of the approximation methods described herein may allow the systems described herein to determine the VFF contributions at the respective locations in near-real-time with high accuracy.

A near-real-time system response, as used herein, means that a computation for approximating the spatio-temporal distribution in response to the received sensor data may be delayed by the time delay introduced, by automated data processing or network transmission, between the occurrence of an event (e.g., receipt of measurement data) and the use of the processed data (e.g., use of the processed data in a diagnostic activity by the medically trained person.) For example, a near-real-time display depicts an event or situation as it existed at the current time minus the processing time, as nearly the time of the live event.

With the above method, near-real-time evaluation of the sensor data provided by the electrode sensors of the catheter can be performed to determine the VFF contribution in an area as defined through the sensor locations of the respective sensors. As a consequence, for each heartbeat interval (ventricular electrical excitation period) the VFF contribution can be derived for a region within the atrium which is reached by the various sensors while the catheter moves through the atrium. Example standard catheters have 64 electrode sensors covering 64 measurement locations in parallel.

It may be desirable to generate a map of the VFF contribution for the entire atrium. However, it may not be possible to scan the entire inner of the atrium within a single heartbeat interval. For this purpose, in one embodiment, the system may receive signals which include signal data recorded over multiple ventricular electrical excitation periods. For example, such data may be provided from an external storage device which records the sensor data while the catheter is being moved through the patient's atrium. It is also possible, that the computer system itself includes such a storage device and records the data being received through the interface component. In this embodiment, the data processing module is further configured to synchronize the selected signal data with the measured electrical excitation events using the reference module. The determination of the spatio-temporal distribution of the Ventricular Far Field is then based on the synchronized signal data. Synchronizing the selected signal data with the measured electrical excitation events, as used herein, means that the electrical excitation event of each heartbeat interval defines the time reference for the signal of the respective ventricular electrical excitation period. That is, all recorded signal data can be projected to the same virtual heartbeat interval referenced to the respective measured electrical excitation event. The approximation method can then be applied to all signal data in the virtual heart beat interval which allows to estimate the spatio-temporal distribution by taking into account all sensor locations which are associated with sensor data of the selected signals, even when being recorded during different ventricular electrical excitation periods.

In some embodiments, the data processing module further includes a model generator to generate a plurality of models wherein each model relates to a particular section within the atrium in combination with a particular time point in relation to the electrical excitation event and reflects a respective approximation of the Ventricular Far Field for the particular section at the particular time point. For example, the particular sections within the atrium can be formed by splitting the volume of the atrium by planes (layers) which are in parallel to the plane forming the boundary between atria and ventricles. The split can be done by using two or more planes which can also have another orientation in space. In addition, more complex forms of spatial models can be applied. Using an appropriate spatial separation into models, the accuracy of the individual distribution mode can be improved and avoids so called over-fitting. Some models (e.g., polynomic models) may not be able to model the entire atrium correctly in a single model. However, in many cases it is possible to correctly model a part of the atrium (e.g., the upper/lower half). In such cases, such sub-models can be trained and used separately.

In some embodiments, the VFF contribution measurement system is part of a diagnosis support system which preprocesses recorded electrogram data before providing the data for further medical diagnostics to a medically trained person or to a computer system trained for atrial disease diagnosis support. In this embodiment, the data processing module further has an Atrial Electrogram Improvement Module (AEIM) to subtract the determined contribution of the Ventricular Far Field at a particular location inside the atrium from the atrial electrogram represented by an electrical signal generated by one of the sensors at the particular location. In other words, for each sensor location where sensor data have been recorded and where the VFF contribution can be determined with the herein disclosed method, the AEIM can eliminate the influence of the VFF contribution in the electrogram. As a result, atrial disease caused signals showing electrical activity of the atrium become detectable (e.g., visible) in the corrected unipolar electrogram especially where such atrial disease cause signals overlap with the disturbing VFF contribution (in the neighborhood of the R wave). Typically, such atrial electrical activity shows an active interval when electrical activity occurs, and a resting interval when no electrical activity occurs. Electrical activity hereby is a consequence of the depolarization of cardiac tissue close to the sensor. No electrical activity occurs when neighboring tissue is in rest and does not depolarize. Thus the electrical activity reflects changes of the transmembrane voltage of adjacent myocardial cells. For example, diagnostic analysis of atrial flutter types can be significantly facilitated by the disclosed signal correction.

In some embodiments, a computer-implemented method is provided for determining Ventricular Far Field contribution in atrial electrograms of a patient. The computer-implemented method can be executed by the modules of the computer system disclosed herein. A computer program with computer readable instructions implementing said modules can be loaded into a memory of the computer system and can be executed by one or more processors of the computer system to cause the computer system to perform the computer-implemented method. In other words, the computer program implements the functions of the respective modules which, in operation, run the computer-implemented method. The respective modules may carryout the functions because the modules include (or have access to) processors, special-purpose computers, digital signal processors, memory, sensors, and the like. The may include receiving a plurality of electrical signals measured by a plurality of sensors wherein the plurality of electrical signals relate to a plurality of locations in an atrium of the patient; determining a reference signal measuring the electrical excitation of the patient's ventricles; selecting from the plurality of the received electrical signals such electrical signals which are recorded under one or more of the following conditions: the respective signals are recorded at locations inside the atrium where the respective sensor has no contact to the atrial tissue, the respective signals are recorded, irrespective of the sensor location, during time intervals where the respective part of the atrium shows no electrical activity, the respective signals are recorded, irrespective of the sensor location, during time intervals which comprise a plurality of heart beat intervals and are subject to subsequent spatial smoothing, and/or determining a spatio-temporal distribution of the Ventricular Far Field inside the atrium by approximating the spatio-temporal distribution based on signal data of the selected signals by using an approximation model.

For example, approximating may use one or more of the following methods: polynomial approximation, approximation with a dipole source model, approximation with a spatio-temporal linear combination of the recorded signal data, approximation performed with Radial Basis Functions, approximation using Look-Up Tables, and/or approximation performed by transforming the signal data to a regular grid before providing it in form of a Look-Up Table.

For example, determining a reference signal may include receiving the reference signal from one or more electrocardiogram sensors measuring at least the R wave of the patient's ventricular electrical activity, receiving the reference signal from a coronary sinus catheter sensor, computing the reference signal from the recorded electrical signal data by blind source separation or analysis of periodicity, and/or determining information about the ventricular contraction by using optical techniques like laser interferometry, pulse oximetry or near-infrared spectroscopy.

In some embodiments, where the plurality of received signals comprises signal data recorded over multiple ventricular electrical excitation periods, the method further includes: synchronizing the selected signal data with the measured electrical excitation events, and determining the spatio-temporal distribution is based on the synchronized signal data.

In some embodiments, determining the spatio-temporal distribution of the Ventricular Far Field further includes: generating a plurality of models wherein each model relates to a particular section within the atrium in combination with a particular time point in relation to the electrical excitation event and reflects a respective approximation of the Ventricular Far Field for the particular section at the particular time point.

In some embodiments, the method further includes: subtracting the contribution of the Ventricular Far Field at a particular location inside the atrium from the Atrial Electrogram represented by electrical signal data measured by a particular sensor at the particular location.

Further aspects of the embodiments described herein will be realized and attained by means of the elements and combinations particularly depicted in the appended claims. It is to be understood that both, the foregoing general description and the following detailed description are exemplary and explanatory only and are not restrictive of the embodiments, as described.

DETAILED DESCRIPTION

Figure 1:
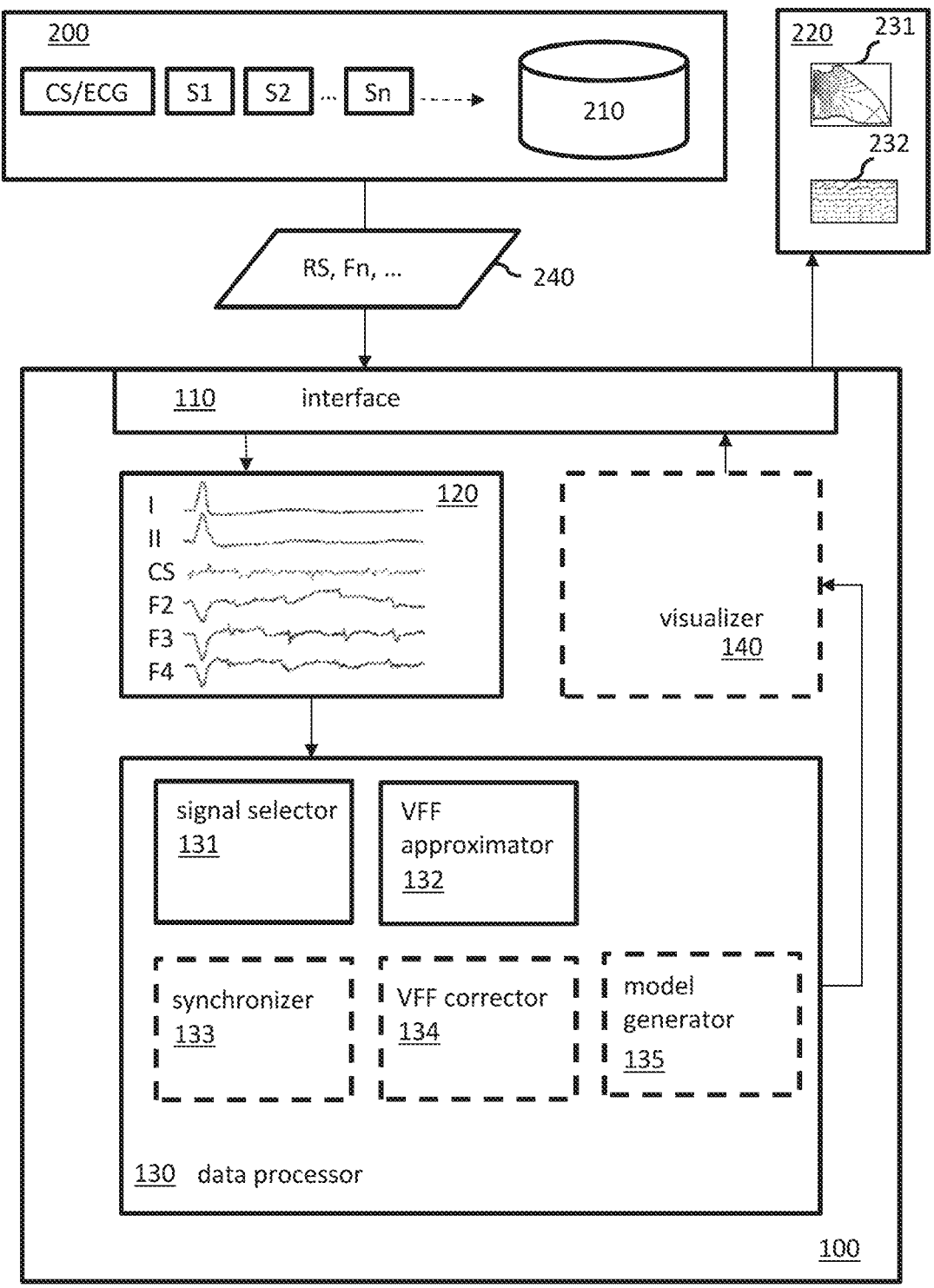
FIG. 1 is a simplified block diagram illustrating an embodiment of a computer system for determining Ventricular Far Field contribution in atrial electrograms of a patient.
Figure 2:
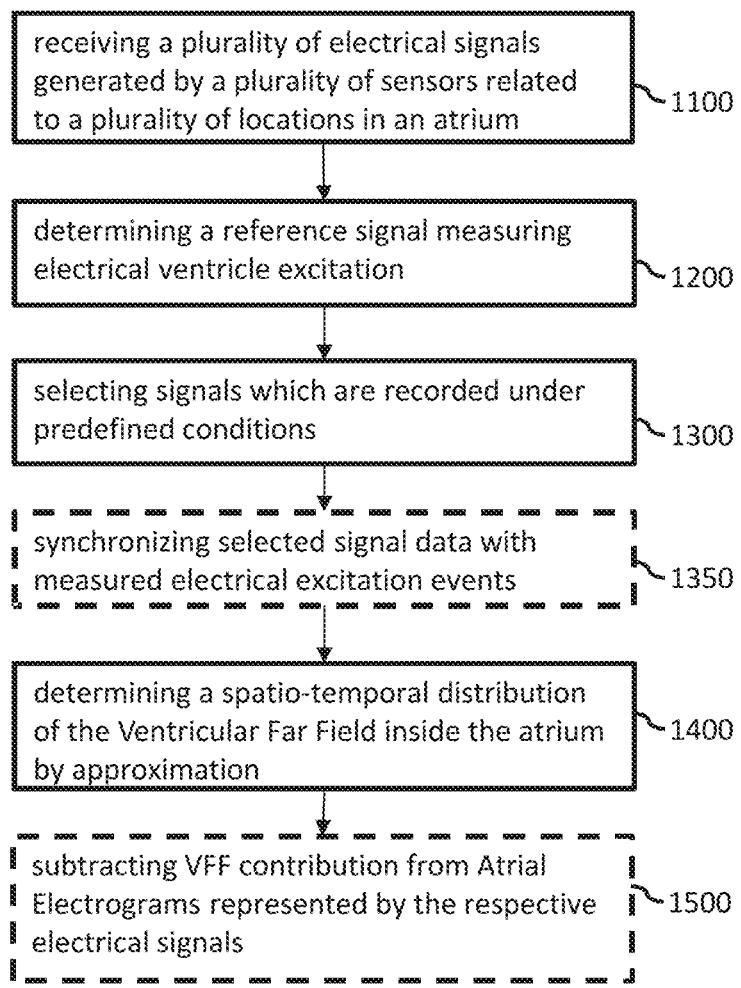
FIG. 2 is a simplified flowchart of a computer-implemented method determining Ventricular Far Field contribution in atrial electrograms of a patient according to an example embodiment.

FIG. 1 is a simplified block diagram illustrating an embodiment of a computer system 100 for determining Ventricular Far Field contribution in atrial electrograms of a patient. FIG. 2 is a simplified flowchart of a computer-implemented method 1000 for determining Ventricular Far Field contribution in atrial electrograms, according to an example embodiment. The functions of system 100 of FIG. 1 are discussed in the context of the method steps of method 1000 which are performed by the respective system components (modules) of system 100. Therefore, the following description refers to reference numbers of the FIGS. 1 and 2.

Figure 4:
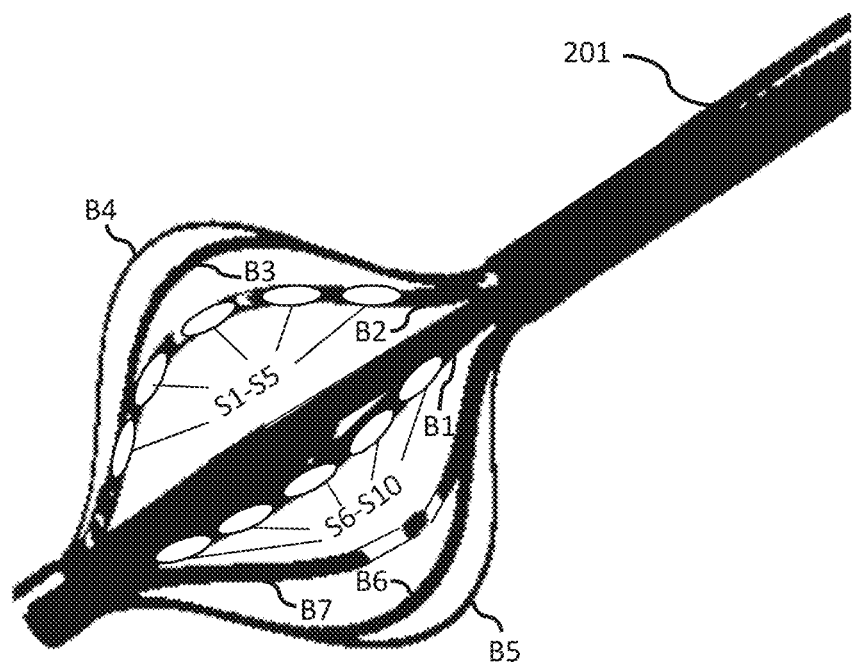
FIG. 4 shows a heart catheter with sensor electrodes.

The system 100 includes an interface component 110 configured to receive 1100 data 240 from one or more external data sources 200. The external data sources may be sensors S1 to Sn providing real time data about the electric activation of a patient's atrium or it may be a data storage device 210 which provides historic (previously recorded or simulated) sensor data about the electric activation of the patient's atria. In the example of FIG. 1, the interface module 110 receives 1100 the electrical signals Fn (F2, F3, F4) measured by respective sensors (e.g., S2 to Sn). Thereby, the measured (recorded) electrical signals F2 to F4 relate to a plurality of locations in the atrium of the patient. In other words, the sensor data F2 is recorded at a particular location which is different from the recording locations of sensor data F3 and F4. Typically, sensors S1 to Sn are electrodes of a multi-polar mapping catheter 201 as illustrated in FIG. 4 (cf. electrodes S1 to S10). Such catheters may be used for electro-anatomical mapping systems EAMS.

Turning back to FIG. 1, the computer system 100 further has a reference module 120 to determine 1200 a reference signal RS (e.g. I, II, CS) reflecting electrical excitation of the patient's ventricles. In the example of FIG. 1, reference signals I, II are reference signals received from one or more electrocardiogram sensors ECG measuring at least the R wave of the patient's ventricular electrical activity. The R wave reflects the electrical excitation event in the patient's ventricles which typically triggers the contraction of the heart. Alternative embodiments may use other reference signals RS if appropriate. For example, the reference signal may be received from a coronary sinus catheter sensor CS. In some embodiments, the reference signal RS may be encoded in the recorded electrograms (e.g., F2 to F4) and can be computed from the recorded electrical signal data by blind source separation or analysis of periodicity. In some embodiments, the reference signal may be determined based on data obtained by respective sensors (not shown) about the ventricular contraction obtained by using optical techniques like laser interferometry, pulse oximetry or near-infrared spectroscopy. The excitation events of the reference signal provide a time reference for the later analysis of the received electrograms. In the example of FIG. 1, the ECG signals I, II show a good indication of the ventricular electrical excitation event and are therefore suitable to be determined as reference signals. The CS signal in the example is less appropriate. In this example, the effect of the excitation event on the sensor signals F2, F3, F4 can be clearly distinguished in the electrograms from other signal contributions. Therefore, the blind source separation or analysis of periodicity methods based on the recorded signals may also be appropriate to determine the reference signal by computation.

Further, the computer system includes a data processing module 130 with a signal selector module 131 to select 1300 from the plurality of the received electrical signals such electrical signals which are recorded at locations inside the atrium where the respective sensor has no contact to the atrial tissue, and/or which are recorded, irrespective of the sensor location, during time intervals where the atrium shows no electrical activity. Both conditions correspond to situations where no atrial activity is measured in the respective electrograms. If the first condition is fulfilled (i.e. there is no contact of the electrodes with the atrial tissue) the sensor electrodes of the catheter are surrounded by blood and no atrial electrical activity is measured. If the second condition (time interval with no electrical activity of the atrium) is fulfilled, atrial tissue contact becomes irrelevant because no electrical activity can be measured as long as no electrical activity occurs. As the atrial activity contribution in the selected signals is negligible they basically measure the VFF contribution at the respective sensor locations. Separating data according to time intervals can be done automatically by analyzing the respective time intervals with regards to signal data indicating atrial electrical activity. Separating signals in relation to locations with or without atrial tissue contact may be achieved by, for example, using a catheter which can measure the contact pressure. In such embodiments, a contact pressure magnitude greater zero indicates tissue contact. In some embodiments, the distance of respective electrodes and the virtual heart anatomy may be measured. In other words, the position of the catheter and its sensor electrodes can be determined for example, by using a Coronary Sinus catheter sensor (CSCS) as a position reference signal source to determine the current position of the electrodes within the atrium while sensor data is recorded. This position can then be marked in a virtual spatial model of the atrium and the distance to the surface elements of the spatial model can be determined by appropriate distance algorithms. A distance greater zero indicates no tissue contact. Position reference, as used herein, means that the position of each further sensor is known relative to the position of the reference sensor. Often, the CSCS may be used as the position reference.

Typically, the locations of a few sensors in the heart are determined via magnet coils mounted at the tip of the catheter and underneath the patient, whereas the other sensors are located using impedance and the principle of potential divider. Once the position of the reference sensor is determined the positions of other sensors are known relative to the position of the reference sensor. If the patient moves, the relative positions can be determined because the movement of the reference sensor is detected. It is also possible to determine the movement of the patient by other means. For example, the movement may be detected by a camera system or by ultrasonic sensors. The detected movement can then be used to re-compute the sensor locations by compensating the movement accordingly. In these implementations, the position reference function of the reference sensor is optional.

Further, the data processor 130 includes a VFF approximator module 132 to determine 1400 a spatio-temporal distribution of the Ventricular Far Field inside the atrium by approximating the spatio-temporal distribution based on signal data of the selected signals. The approximation method can be a polynomial approximation, an approximation with a dipole source model, an approximation with spatio-temporal linear combination of the recorded signal data, approximation performed with Radial Basis Functions, approximation using Look-Up Tables, and/or approximation performed by transforming the signal data to a regular grid before providing it in form of a Look-Up Table.

An example of polynomial approximation is to use a polynomial that describes the value of the VFF potential in dependency of the spatial coordinates (like Cartesian coordinate system with coordinates x, y, z or the Polar coordinate system spatial coordinates r, φ, □) for each point in time. The degree of the polynomial can be chosen to minimize the residual of approximation for the measured signal data. A least-squares-fit can be used to estimate the coefficients of the polynomial.

An example of a linear polynomial model (second order) can be expressed by the following formula:

$$\begin{pmatrix} \phi_1 \\ \phi_2 \\ \dots \\ \phi_M \end{pmatrix} = \begin{pmatrix} 1 & x_1 & y_1 & z_1 & x_1y_1 & x_1z_1 & y_1z_1 & x_1^2 & y_1^2 & z_1^2 \\ 1 & x_2 & y_2 & z_2 & x_2y_2 & x_2z_2 & y_2z_2 & x_2^2 & y_2^2 & z_2^2 \\ \dots & \dots & \dots & \dots & \dots & \dots & \dots & \dots & \dots & \dots \\ 1 & x_M & y_M & z_M & x_My_M & x_Mz_m & y_Mz_M & x_M^2 & y_M^2 & z_M^2 \end{pmatrix} \begin{pmatrix} c_0 \\ c_x \\ c_y \\ c_z \\ c_{xy} \\ c_{xz} \\ c_{yz} \\ c_{x2} \\ c_{x2} \\ c_{y2} \\ c_{z2} \end{pmatrix}$$

Formula 1 with subscripts 1 to M indicating the respective measurements; x, y, z are the spatial coordinates, and cX are the coefficients of model component X. φ are the resulting potentials at the measurement positions. The coefficients are determined during model generation.

An example of a dipole source model approach is to place multiple dipoles in space and adapt their strength to compute a potential field which approximates the measured signal data. The dipoles may be located in the atria, in the ventricles, and/or surrounding region. If for example the location of dipoles should reflect the position of the ventricles, this position can either be known from intracardiac mapping using an EAMS or by additional imaging techniques like computed tomography or magnetic resonance imaging or based on a statistical model of cardiac shape. The dipoles of the dipole source model may be located in the convex hull of the cardiac chambers or at the tissue blood boundary or in the tissue or other locations. The strength of each dipole in each spatial direction can be adapted so that the resulting potential field approaches the measured signal data. Approximation can be done by using a least-squares-approximation. Alternatively, the method of Tikhonov regularization can be applied to constrain the strength of individual dipoles and to prevent over-fitting. Additional dipoles may be located in the atrium, generating a model to explain both local atrial and VFF components. An example of dipole source model can be expressed by the following formula:

$$\Phi(\vec{r}) = \frac{1}{4\pi\kappa} \left[ \frac{(\vec{r} - \vec{r_p})}{|\vec{r} - \vec{r_p}|^3} \right] \cdot J_i(\vec{r_p})$$

Formula 2 with r being the measurement position in space, rP being the position of the dipole P in space, J being the impressed current density of dipole P, and κ being the conductivity.

An example of a spatio-temporal linear combination is the so-called principal component analysis, which can be used to remove random noise from the signals and focus on dominant signal components. Another spatio-temporal linear combination is the weighted average of selected signals for each point in time. By computing the approximation model on the basis of the selected signal data, interpolation and extrapolation of the VFF contribution is possible. Therefore, there is no need for sensor data recorded at locations with atrial tissue contact. Rather, the VFF contribution at such locations can be extrapolated from the determined spatio-temporal distribution.

Figure 11:
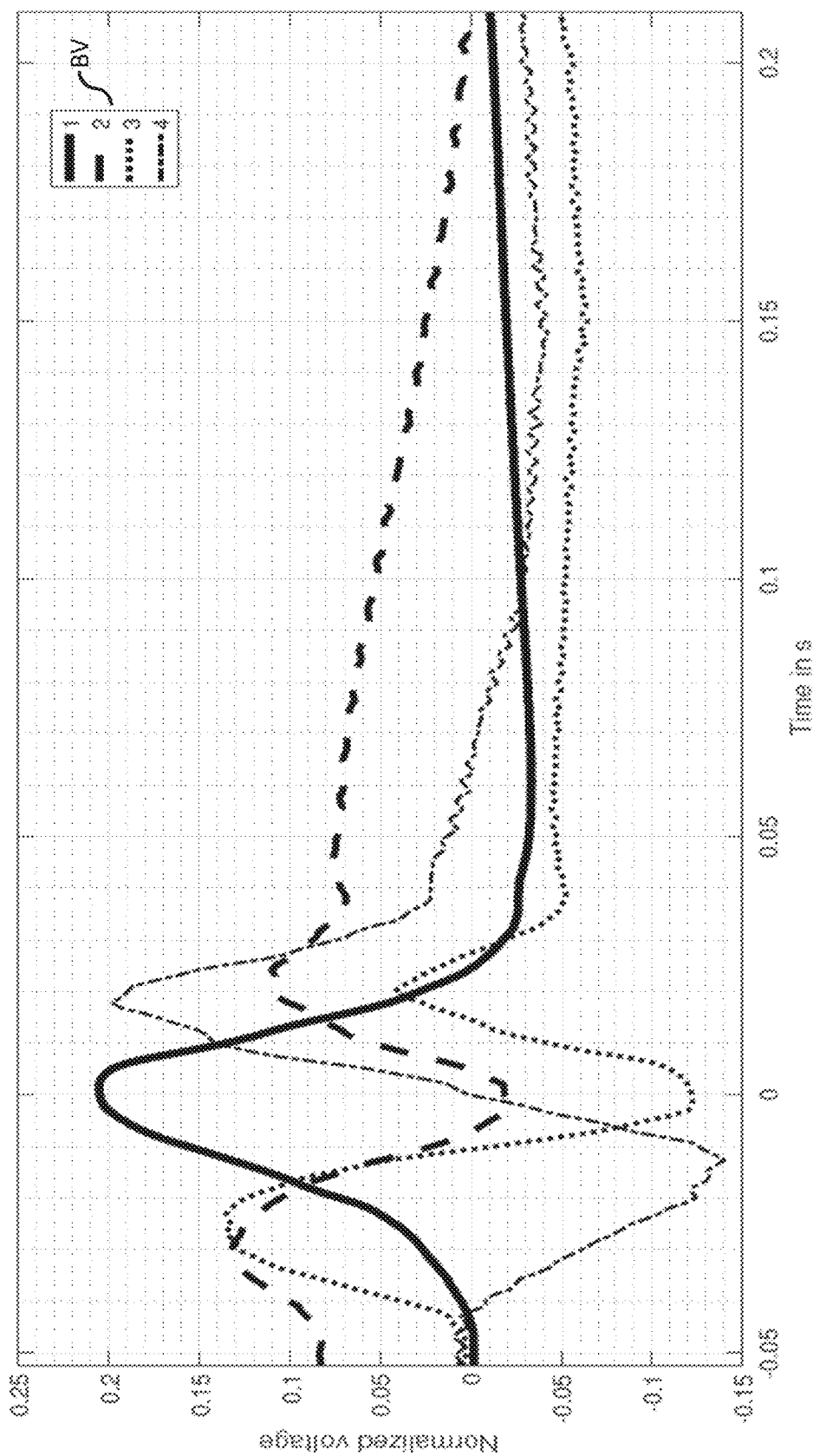
FIG. 11 illustrates an example of a temporal approximation model with four basis vectors.

Turning briefly to FIG. 11, this figure illustrates an example of a temporal model TM1 which is generated as a basis system reflecting the temporal VFF course. This basis system can be based on signal segments associated with electrodes that are far enough away from the atrial wall so that the signals are not disturbed by the atrial component, and analyzed using the so-called principal component analysis. Each basis vector has a duration of the time interval in which the VFF contribution should be removed (e.g., a 250 milliseconds time interval associated with the R wave). From signal theory, the first basis vector describes the template VFF signal, and together with the second and a few more basis vectors, all VFF signals anywhere in the atrium can be described by an appropriately chosen linear combination of the basis vectors. Advantageously, the number of basis vectors is in the range of 1 to 10. The example of FIG. 11 shows a temporal model using four basis vectors BV (1, 2, 3, 4). Measured signals, synchronized to the VFF window, can now be approximated by this temporal basis system TM1 using a Least Squares approach. The obtained estimate for the VFF contribution can subsequently be subtracted from the measurement to get a corrected signal showing the atrial signal without the disturbance caused by the VFF contribution. In other words, the signal components orthogonal to the temporal VFF basis are considered to represent the pure atrial signal.

Turning back to FIG. 1, in one embodiment, the system 100 includes a visualizer component 140 which is configured to render a graphic representation 231 of the spatio-temporal distribution. The graphic representation can be displayed to a medically trained person for diagnosis support through a display device 220 which is communicatively coupled with the computer system 100 through the interface 110.

In some embodiments, the system 100 includes a synchronizer component 133 which is used in situations where the plurality of received signals includes signal data recorded over multiple ventricular electrical excitation periods. This is typically the case when the catheter is moved to multiple measurement locations within the patient's atrium for recording respective sensor data. It is to be noted that while recording sensor data the catheter is not moved. In this example, the selected signal data is synchronized 1350 with the measured electrical excitation events. In other words, a particular electrical excitation event of the heart serves as the time reference for the recorded signals which are recorded during the respective heart beat interval. The signal data recorded over multiple heartbeat intervals can thus be projected into one interval where the respective excitation event defines the start point of the interval. In this embodiment, the spatio-temporal distribution is determined based on the synchronized signal data. The VFF contribution can thus be determined 1400 by using all selected measurement data recorded over a period of time during which the catheter was moved through the patient's atrium. By using the approximator 132 functions for interpolation and extrapolation a continuous model of the VFF contribution may be generated for the entire inner of the atrium.

In some embodiments, the system 100 may further include a model generator 135 to generate a plurality of models wherein each model relates to a particular section within the atrium in combination with a particular time point in relation to the electrical excitation event. Such a model reflects a respective approximation of the Ventricular Far Field for the particular section at the particular time point. For example, the model sections may correspond to virtual layers within the atrium.

In some embodiments, the system 100 includes an atrial electrogram improvement module 134 also referred to as VFF corrector 134. The VFF corrector subtracts 1500 the contribution of the Ventricular Far Field at a particular location inside the atrium from the Atrial Electrogram represented by an electrical signal generated by one of the sensors S1 to Sn at the particular location. As a result, the VFF contribution is removed from the respective atrial electrograms and the visibility of the signals of interest for medical diagnosis is improved in the atrial electrograms.

Figure 3A:
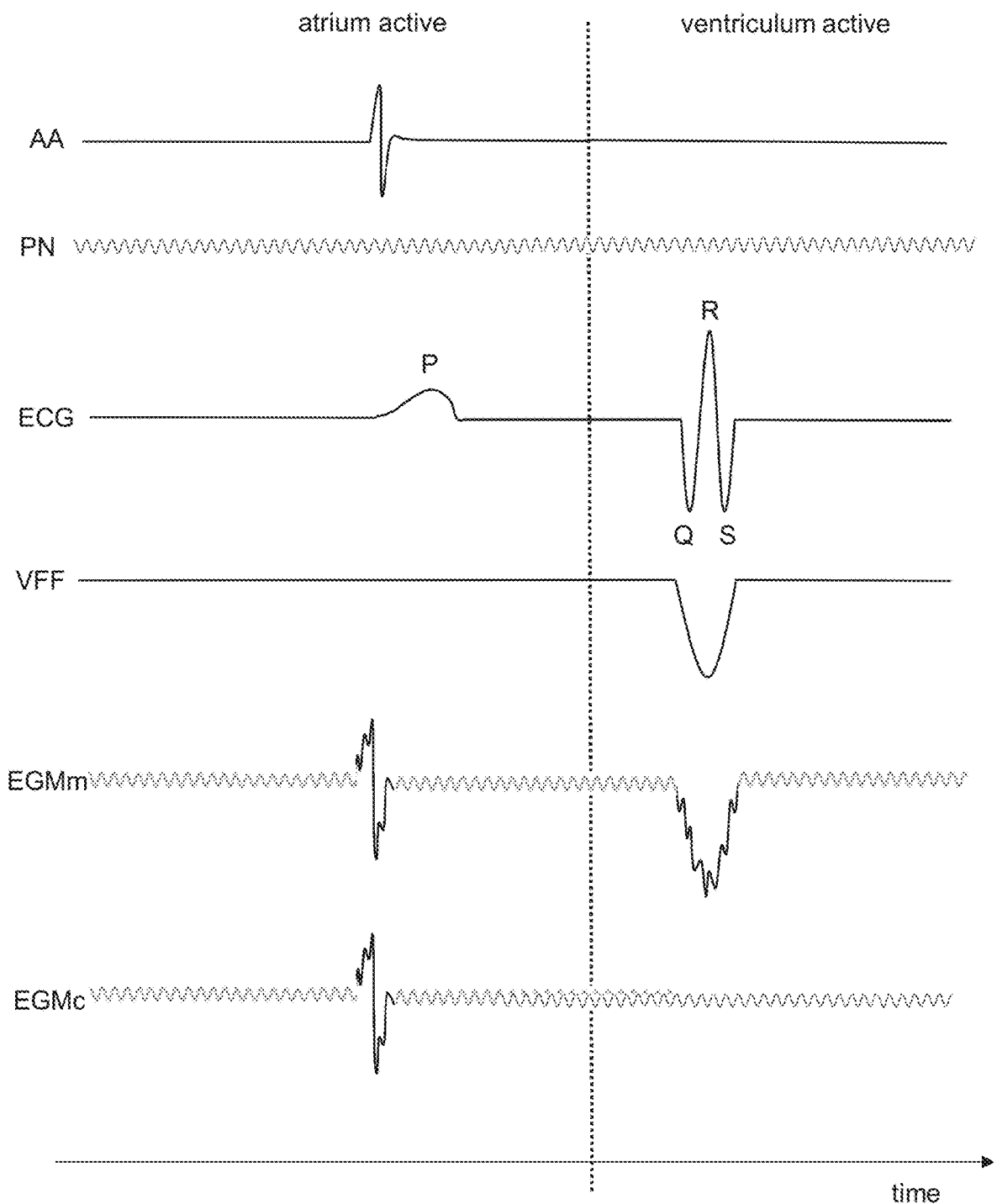
FIG. 3A is a schematic illustration of signal contributions in a unipolar atrial electrogram before and after correction.
Figure 3B:
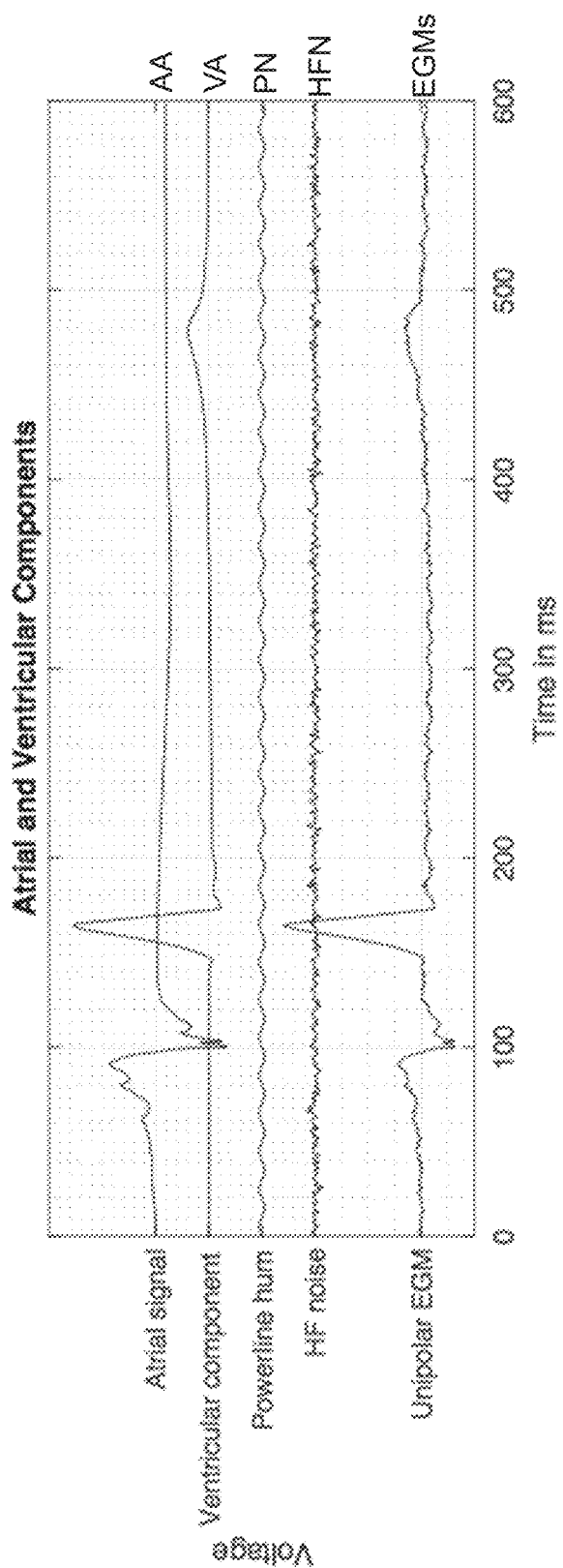
FIG. 3B shows a simulation of signal contributions in a unipolar electrogram.

FIGS. 3A and 3B illustrate the function of the VFF corrector. FIG. 3A is a schematic illustration of signal contributions in a unipolar atrial electrogram (UAE) before and after correction. In the left part of the figure (left to the dotted vertical line), signals are shown which occur during the period where the atrium is active. In the right part of the figure, signals are shown during the period where the ventriculum is active. For each signal, the momentary signal value corresponds to a voltage which can be measured by the respective sensors. The signal AA shows the UAE contribution of the atrial activity of an atrium. The shown signal curve is a typical curve which is expected at a particular sensor location. The signal PN illustrates the powerline noise (e.g., 50 Hz) which superimposes the AA signal. The ECG signal illustrates the ventricular activity of the heart with the so-called P, Q, R, and S waves. The QRS waves are the root cause of the Ventricular Far Field VFF which can be observed in the atrium and which also superimposes the UAEs. The EGMm signal schematically illustrates a measured UAE with signal contributions from the AA, PN and VFF signals. A goal is to eliminate the VFF contribution from EGMm as illustrated in the corrected UAE for the signal AGMc.

FIB. 3B shows simulated signals over a time period of 600 milliseconds which have a more realistic signal shape (Voltage) than the schematic signal illustrations in FIG. 3A. The Atrial signal AA corresponds to the atrial activity of the atrium. The Ventricular component VA shows the VFF contribution to the UAE (Unipolar EGM). It is to be noted that the VFF contribution can result in a negative Voltage peak (cf. FIG. 3A) or in positive Voltage peaks dependent on how the voltage is measured. The Powerline hum PN corresponds to the PN noise curve in FIG. 3A. In addition, HF noise HFN is present in a real UAE. The EGMs signal illustrates the aggregate UAE which results from the signal contributions of the signals above. In cases where the VFF contribution interferes with the AA signal the AA signal information becomes invisible in the measured EGM signal because the VFF contribution dominates the aggregate signal in a way that it becomes meaningless for diagnostic analysis purposes.

FIG. 4 shows a heart catheter 201 with sensor electrodes S1 to S10. Sensor electrodes S1 to S10 are only illustrated for two (B1, B2) of the catheter branches B1 to B7. However, each branch is equipped with a plurality of sensor electrodes. Such catheter sensors are typically used inside the atrium and moved through the atrium to measure the atrial activity by making a contact between the sensors S1 to S10 and the atrial tissue of the patient. It is clear that typically only a subset of the sensors can make contact with the atrial tissue at a given point in time. When the catheter 201 is moved through the patient's atrium, at least a subset of the sensor electrodes is always entirely surrounded by blood (i.e. such electrodes which have no contact with the atrial tissue). It can also happen that no sensor electrode has a contact with the atrial tissue at a given point in time. In normal EGM analysis the measurement values provided by the sensors S1 to S10 without having contact with the atrial tissue are discarded, as they do not carry useful information with regards to the atrial activity. However, such measurement data is used by the disclosed method for determining the VFF contribution at respective locations.

Figure 5:
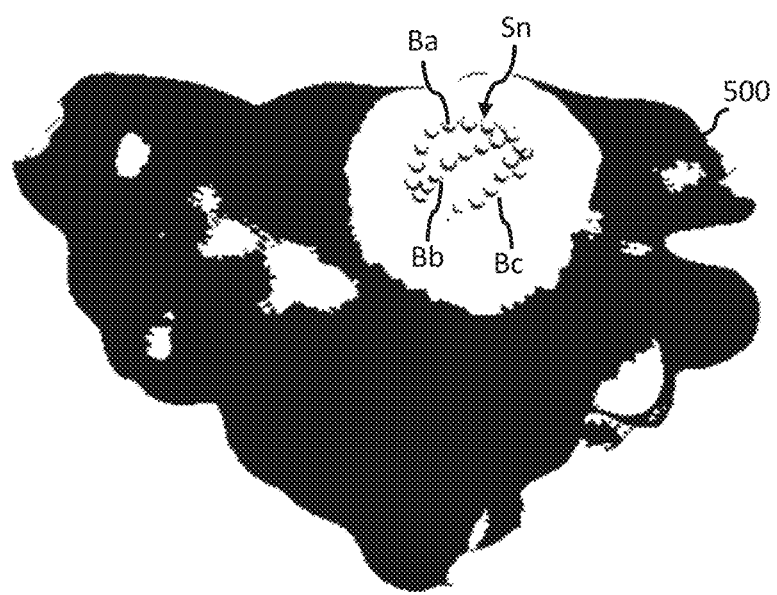
FIG. 5 illustrates an atrium with a catheter inside the atrium and some respective sensor electrodes.

FIG. 5 illustrates, at a particular point in time, an atrium 500 with a catheter inside the atrium and some respective sensor electrodes Sn. The catheter is placed in such a way that the sensor electrodes Sn of three branches Ba, Bb, Bc are in contact with the atrial tissue whereas the sensor electrodes mounted on the neighboring or opposite branches are surrounded by blood and are not shown in the figure.

Figure 6A:
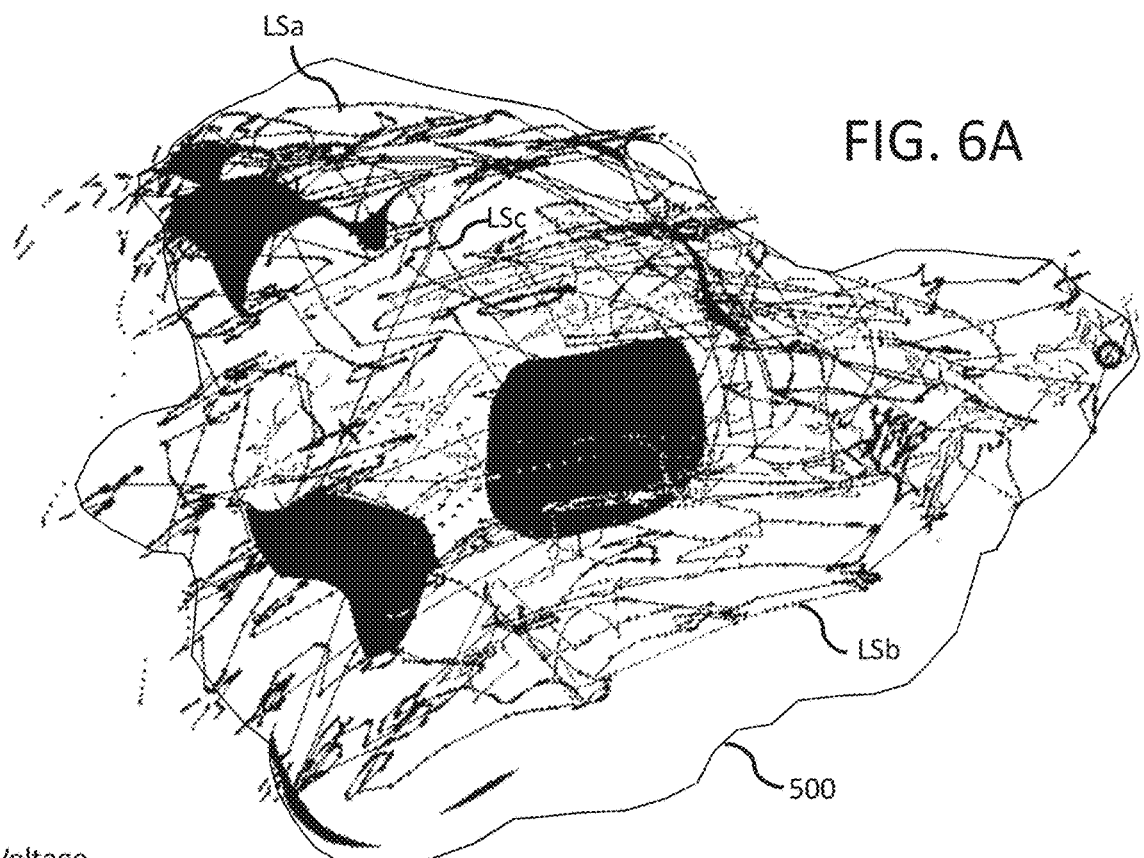
FIGS. 6A, 6B show traces of sensor electrodes of a heart catheter being moved through an atrium.
Figure 6B:
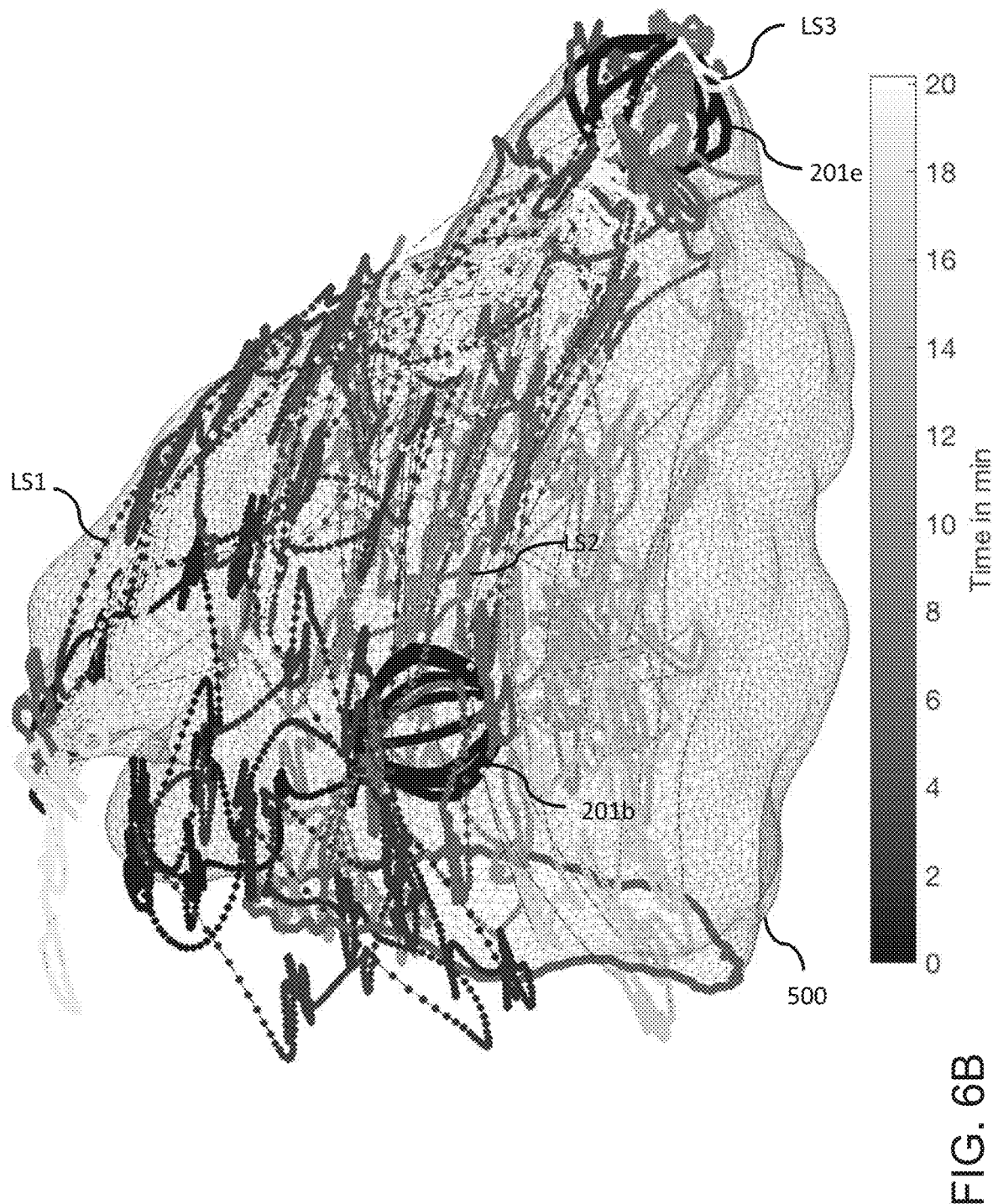

FIGS. 6A and 6B show traces of an electrode sensor of a heart catheter being moved through an atrium 500. In FIG. 6A, each dot on a trace represents a sensor location at which measurement data was recorded and synchronized. For example, location LSa is a location close to the upper bound (roof) of the atrium 500. LSb is a location close to lower bound (valve plane) of the atrium and LSc is a location closer towards the center of the atrium 500. In the example, locations of measurement data outside the atrium 500 (for example, the trace portions which are located left from the atrium boundary) result from particular conditions during the measurement. In those cases the catheter was pushed against the atrial tissue (for example to get as many electrodes as possible into contact with the atrial tissue). The pressure which was applied during the measurement caused some stretch of the atrial tissue so that the recorded measurement data appear outside the atrial boundaries which were extended to the respective measurement locations during the measurement. However, after the measurement data was recorded the atrial tissue retracted to its normal position once the pressure was released. At each point in time the catheter can simultaneously record signal data provided by the electrode sensors mounted on the various branches. That is, signal data being recorded simultaneously reflect signal data at different locations but during the same heart beat interval. However, the number of locations in FIG. 6A is recorded over a longer time period (e.g. 20 minutes/ 1200 seconds). That is, most measurement data is recorded at different points in time which also belong to different heart beat intervals.

A catheter typically includes a plurality of electrode sensors (cf. FIG. 4). FIG. 6B illustrates traces of one electrode sensor using a grey scale to illustrate the measurement time points for the respective sensor locations. The catheter positions at the beginning and at the end of the measurement are visualized by the catheter shape representations 201b and 201e, respectively, to provide an impression of the size of the area which can be covered by the electrodes of the catheter at any given point in time. In other words, for this area the sensor electrodes record measurement data for different sensor locations (i.e. the locations of the respective electrodes) in parallel. That is, for this area measurement data can be simultaneously recorded in relation to the same heartbeat interval. In the example, the first sensor location LS1 is illustrated as a black bullet which indicates that the measurement has been made during the first sixty seconds of the measurement period. The measurement data recorded at the second sensor location LS2 was recorded approximately after nine minutes (e.g., 540 seconds), and the measurement data recorded at the third sensor location LS3 was recorded approximately after 20 minutes (e.g., 1200 seconds) towards the end of the measurement period.

Figure 7:
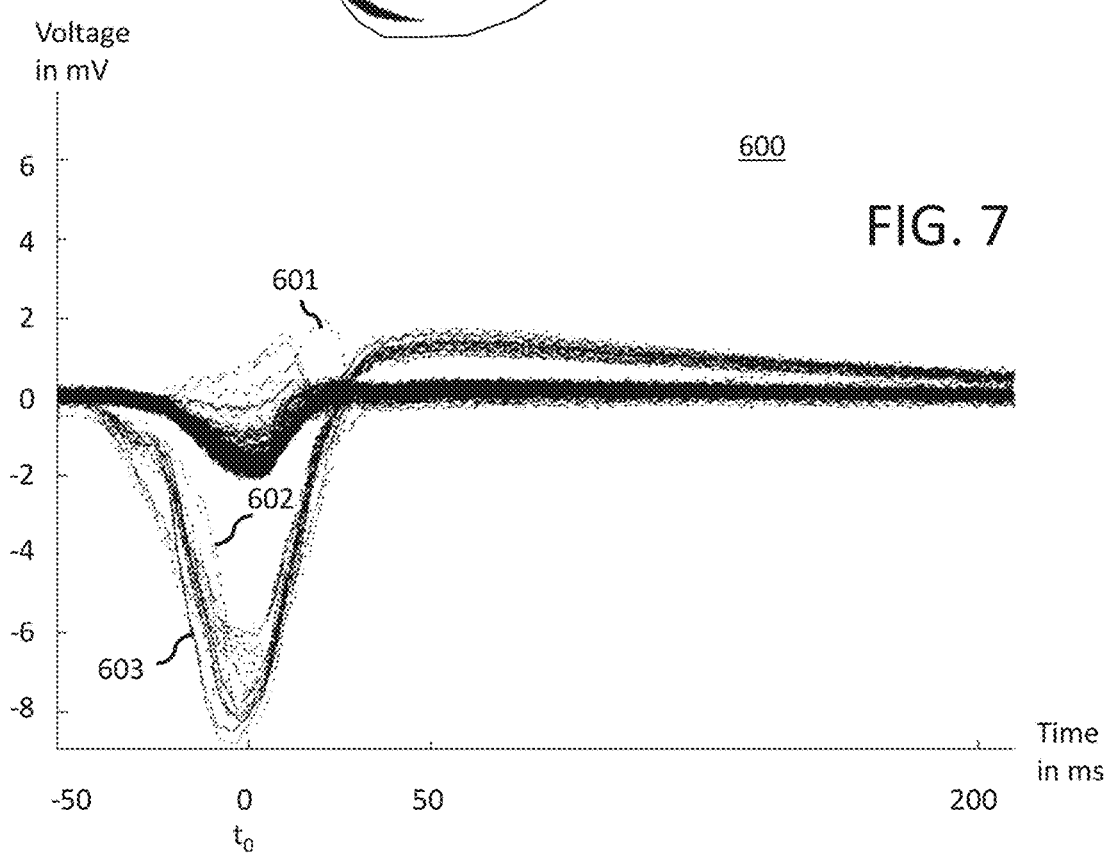
FIG. 7 shows an example of synchronized selected signals as captured by an embodiment of the computer system.

FIG. 7 shows an example of synchronized selected signals 600 as captured by an embodiment of the computer system. The figure illustrates measurement data recorded at a plurality of different sensor locations (e.g., the sensor locations of the traces in FIG. 6A or 6B) and for different heart beat intervals. Thereby, each curve of the measurement data (e.g., curve 601, 602, 603) relates to a particular sensor electrode signal recorded a respective location during a respective heartbeat interval. The synchronizer of the computer system can use a reference signal (e.g., the peak of the R wave) of each heartbeat interval to define the time point zero for the respective heartbeat interval. All measurement data can thus be superposed into the same time interval starting with the common sync time point 0. The synchronized selected signals in FIG. 7 can be handled in the same way like the sensor signals of the sensor electrodes being recorded simultaneously during the same heartbeat interval. That is, the synchronized selected signals correspond to a snapshot of the atrium where all measurement data at the respective locations were recorded during the same heartbeat interval. The basic assumption thereby is that the signal behavior at each location is substantially the same after the sync point t0 for each heartbeat interval.

Whereas the real simultaneous measurement data of the electrodes of the catheter during a single heartbeat interval (while the catheter is at a particular location) allow to compute the VFF contribution for the atrium section covered by the electrodes during this heartbeat interval in near-real-time, the synchronized selected signal data allows to determine the VFF contribution after the end of the measurement period (i.e. offline) for the entire section covered by all sensor locations used during the measurement period (e.g., 10 to 30 minutes/600-1800 seconds).

Figure 8:
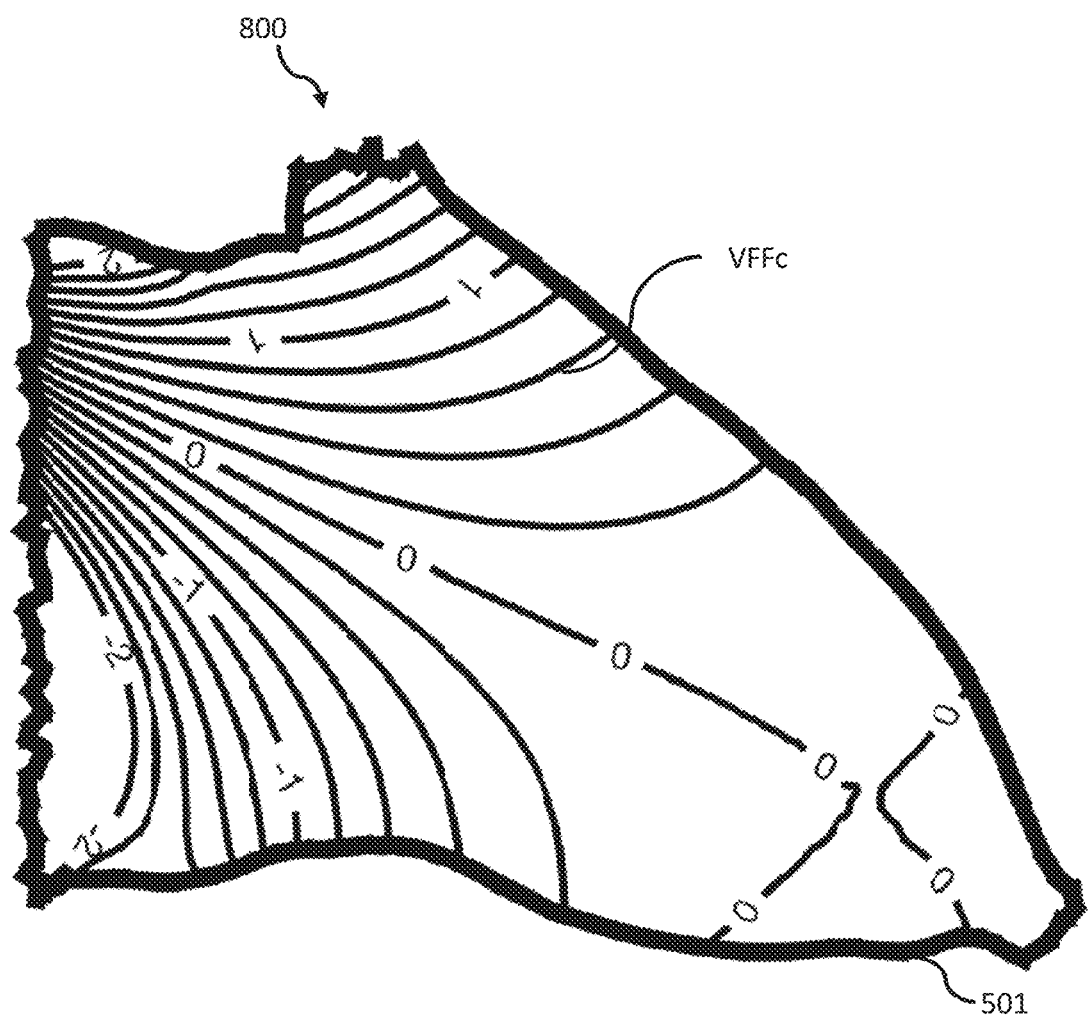
FIG. 8 illustrates a spatio-temporal distribution of the Ventricular Far Field contribution at a particular point in time in an atrium.

FIG. 8 illustrates a spatio-temporal distribution 800 of the Ventricular Far Field contribution VFFc at a particular point in time for one layer 501 of the atrium. The VFF contribution can be determined for multiple layers of the entire atrium based on synchronized selected signals from a plurality of sensor locations which are reached by moving the catheter through the atrium during a longer measurement period. Sensor locations in the proximity of the selected layer contribute to the VFFc computation of this layer.

However, the proposed approximation methods can also be applied to the measurement data provided by the catheter electrodes during a single heartbeat interval. This allows to determine in near-real-time VFF contributions as a spatio-temporal distribution for the section of the atrium which is covered by the catheter electrodes during this heartbeat interval. In other words, the corrections of the respective UAEs can be performed in near-real-time for such subsections of the atrium while the catheter is being moved through the patient's atrium.

Turning back to the simulated selected signals scenario illustrated in FIG. 8, the amplitude of the VFF contribution VFFc at the respective locations of the layer 501 at a particular time point is visualized. Amplitude values around zero millivolts are measured at the lower right part of the layer 501 in the figure, representing the right superior pulmonary vein. Higher amplitude values (greater than 2 millivolts in magnitude) are measured at the upper left and lower left layer sections in the figure, being located closer to the mitral valve. By using any one of the methods: polynomial approximation, approximation with a dipole source model, approximation with a spatio-temporal linear combination (e.g., principal component analysis), approximation performed with Radial Basis Functions, approximation using Look-Up Tables, and approximation performed by transforming the signal data to a regular grid before providing it in form of a Look-Up Table for approximating the spatio-temporal distribution 800 based on signal data of the selected signals a continuous spectrum of VFFc voltage values can be computed. Extrapolation allows to also compute values for the atrial tissue surface. A person skilled in the art may use other approximation methods which are appropriate in the described context.

In more general terms, a plurality of models can be generated wherein each model relates to a particular section (e.g., layer 501) within the atrium in combination with a particular time point in relation to the electrical excitation event. Such a model reflects a respective approximation of the Ventricular Far Field for the particular section at the particular time point.

Figure 9A:
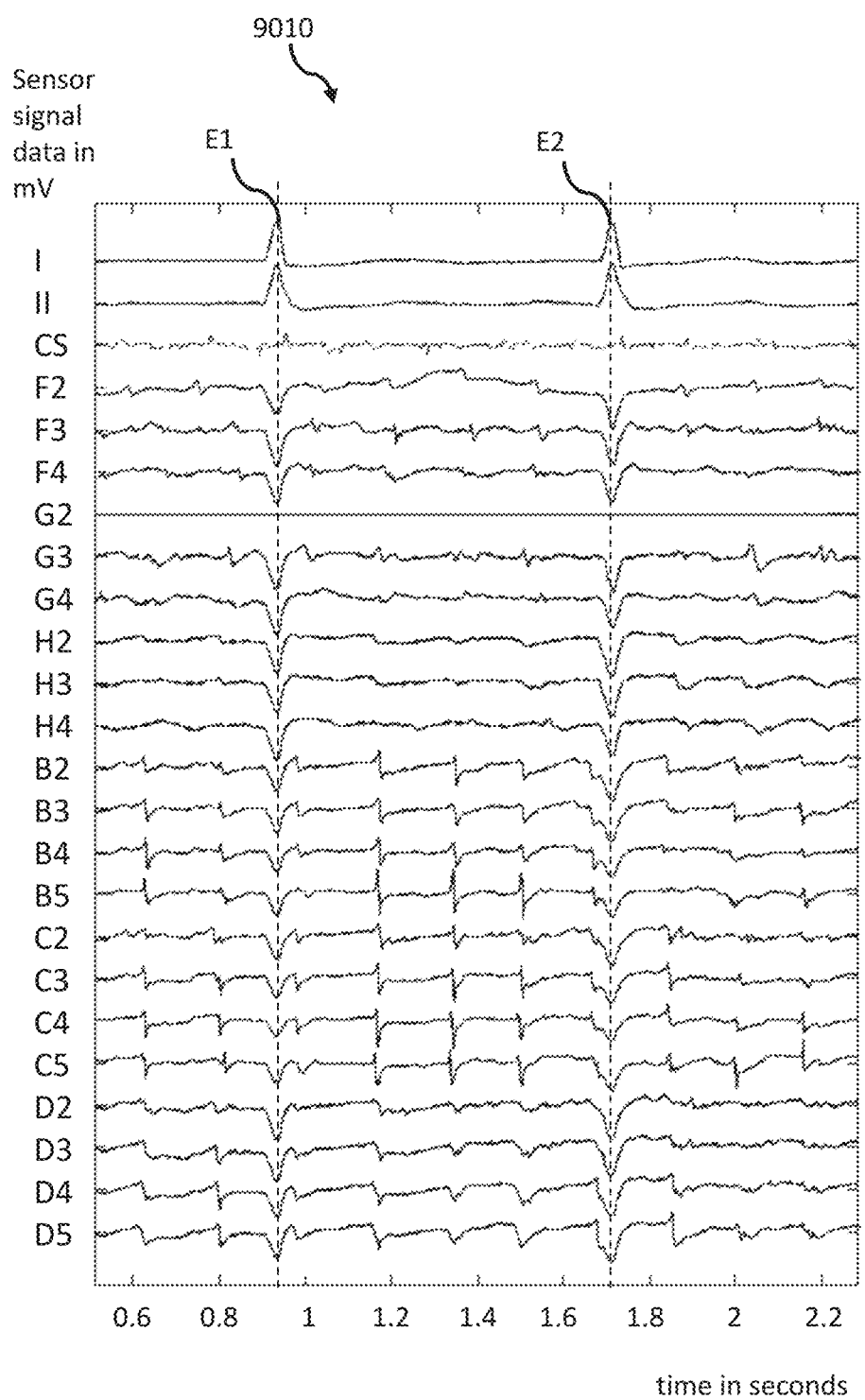
FIG. 9A shows an example of recorded reference signals and selected electrogram signals.

FIG. 9A shows a real world example 9010 of recorded reference signals and selected electrogram signals. The signals I, II show the R-wave of the patient's ventricular activity defining the excitation events E1, E2 which can later on be used as reference signals for the synchronization of the unipolar atrial electrograms across multiple heartbeat intervals.

The CS signal corresponds to the signal of a coronary sinus sensor and is not relevant for this example. The signal G2 corresponds to a broken electrode of the catheter. The other signals (F*, G*, H*, B*, C*, D*) correspond to signals recorded by the electrode sensors of the respective branches of the catheter. The impact of the VFF in the Unipolar atrial electrograms is clearly visible at the times the excitation events E1, E2 occur (about 0.94 seconds and 1.7 seconds, respectively).

Figure 9B:
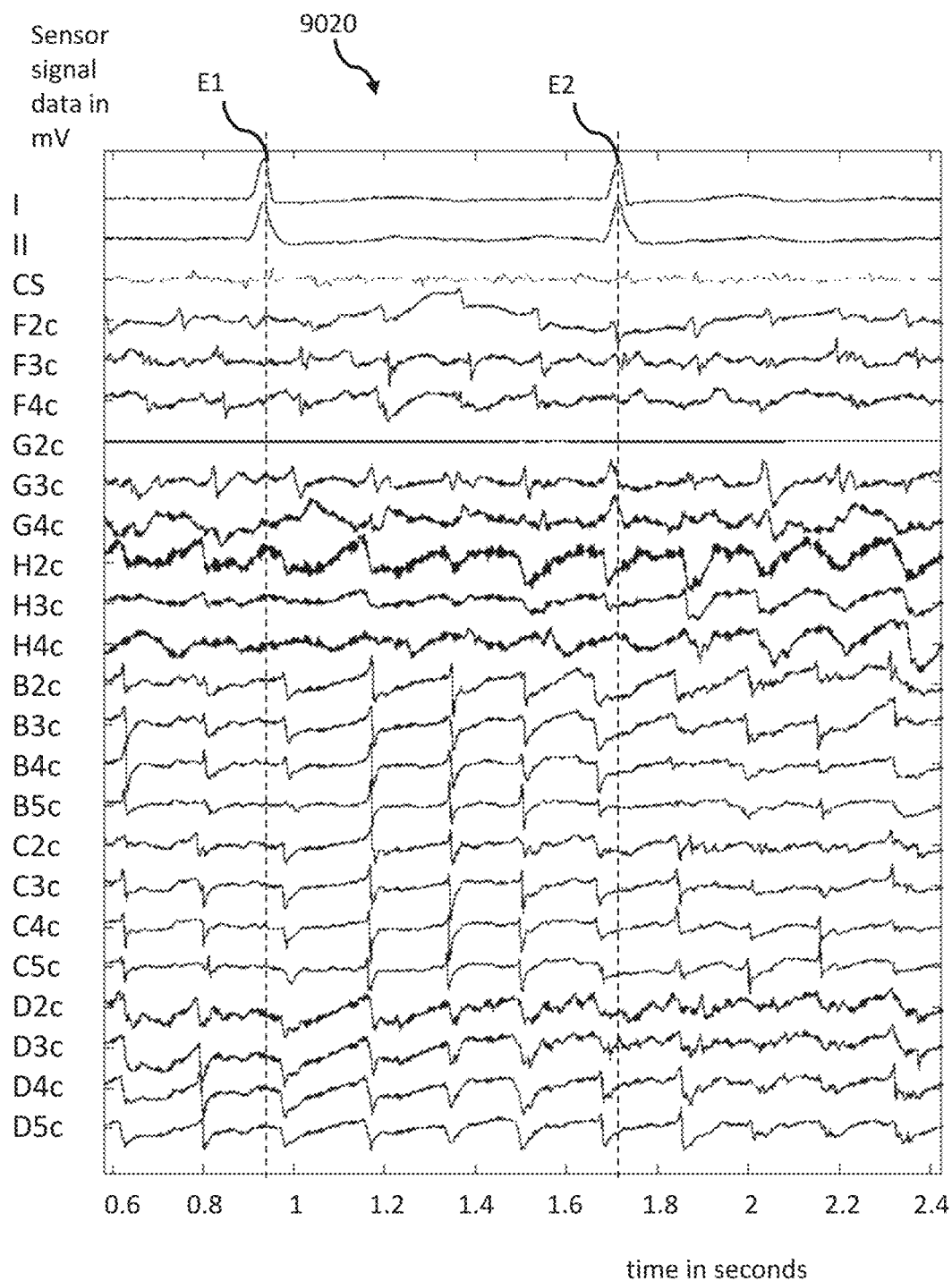
FIG. 9B shows an example of the corrected electrograms according to an embodiment.

FIG. 9B shows a real world example of the corrected electrograms 9020 according to an embodiment. The corrected UAEs (F*c, G*c, H*c, B*c, C*c, D*c) are derived by subtracting the VFF contribution from the original UAEs in FIG. 9A once the VFF contribution has been determined in accordance with the method disclosed herein.

Figure 10:
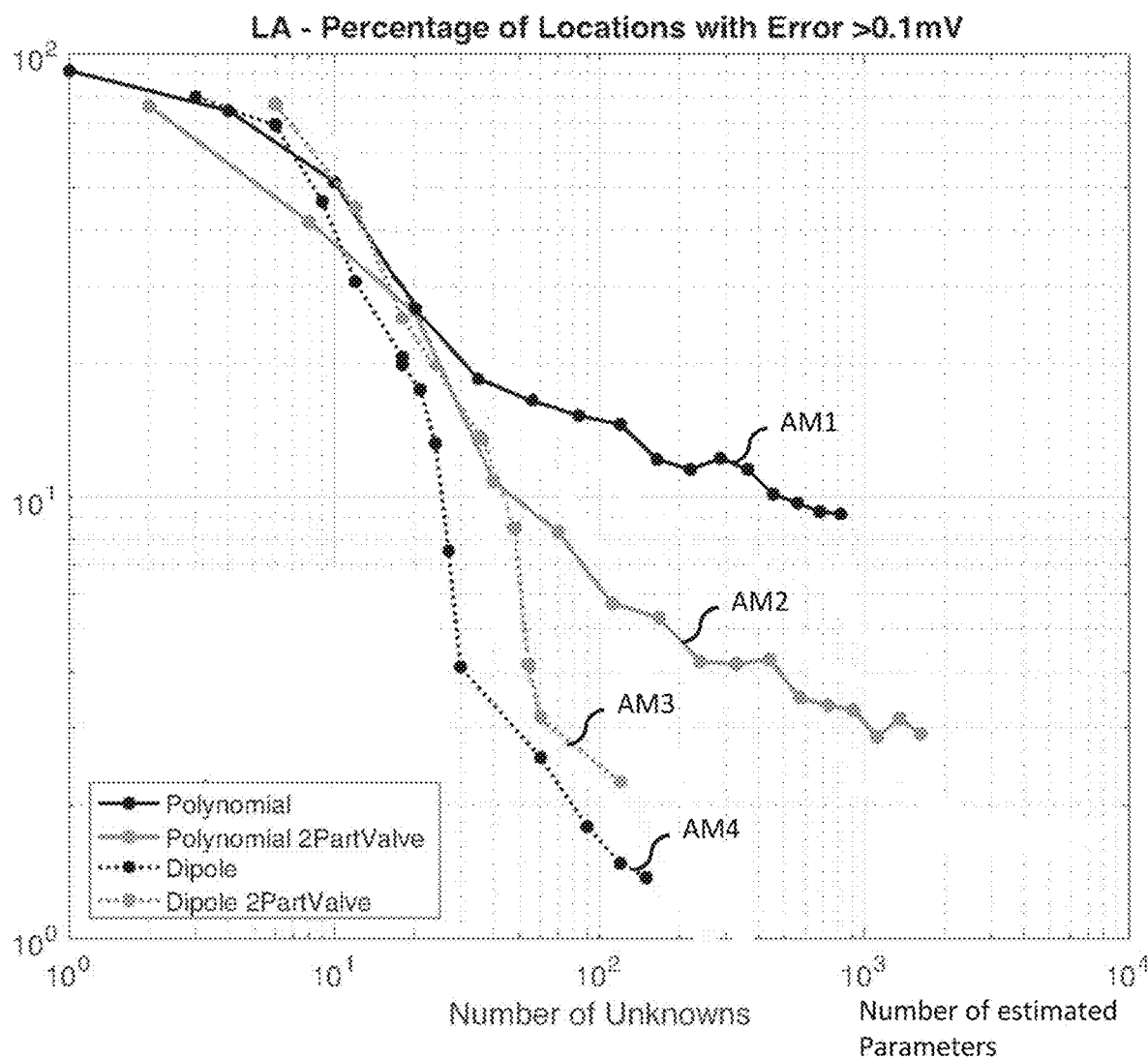
FIG. 10 illustrates different performances of different approximation methods for determining the VFF contribution.

FIG. 10 illustrates different performances of different approximation methods for determining the VFF contribution. The horizontal axis shows the number of estimated Parameters (number of unknowns) which corresponds to the complexity of the model. The vertical axis shows the percentage of not perfectly estimated data points. Not perfectly estimated in this context means that the estimate is worse than some specified threshold.

The curves show the performance for two approximation methods: the Dipole method (AM3, AM4) versus the Polynomial method (AM1, AM2). The Dipole method (AM3, AM4) shows a better performance than the Polynomial method (AM1, AM2).

For the Polynomial method the curve AM1 is the result of an approximation using a single model for the entire atrium whereas the curve AM2 is the result for an approximation based on two sub-models which are separated by a plane parallel to the plane between the atria and ventricles (valves). For this method, the approach using two sub-models provides better performance.

For the Dipole method the curve AM4 is the result of an approximation using a single model for the entire atrium whereas the curve AM3 is the result for an approximation based on two sub-models which are separated by a plane parallel to the plane between the atria and ventricles (valves). For this method, the single model approach provides slightly better performance.

Figure 12:
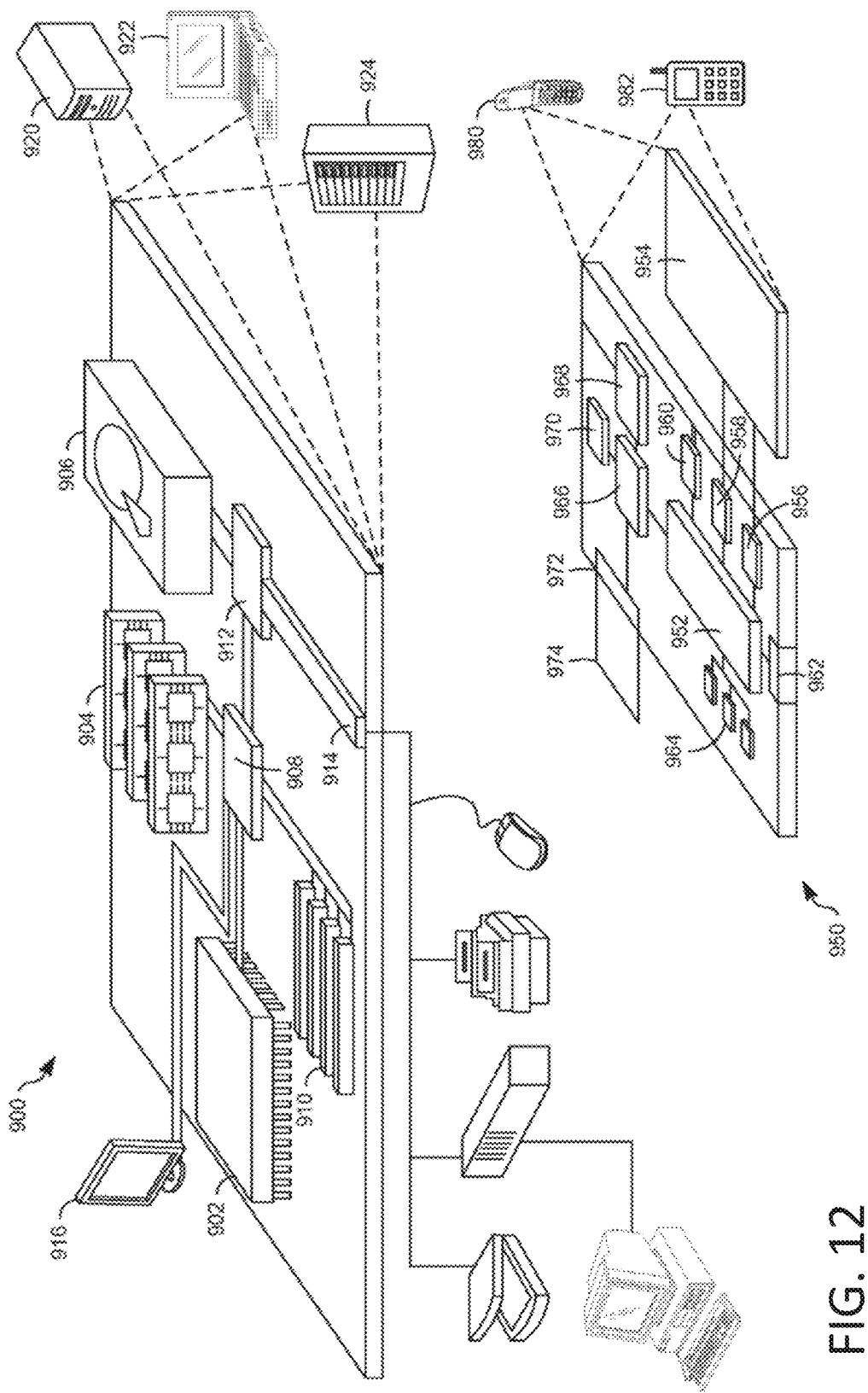
FIG. 12 is a diagram that shows an example of a computer device and a mobile computer device which may be used with the techniques described herein.

FIG. 12 is a diagram that shows an example of a computer device 900 and a mobile computer device 950, which may be used with the techniques described here. Computing device 900 is intended to represent various forms of digital computers, such as laptops, desktops, workstations, personal digital assistants, tablets, servers, blade servers, mainframes, and other appropriate computers. Generic computer device 900 may correspond to a computer system 100 as illustrated in FIG. 1. Computing device 950 is intended to represent various forms of mobile devices, such as personal digital assistants, cellular telephones, smart phones, and other similar computing devices. For example, computing device 950 may be used by a user as a front end to interact with the computer system 100. Computing device may, for example, include the display device 220 of FIG. 1. The components shown here, their connections and relationships, and their functions, are meant to be exemplary only, and are not meant to limit implementations of the embodiments described and/or claimed in this document.

Computing device 900 includes a processor 902, memory 904, a storage device 906, a high-speed interface 908 connecting to memory 904 and high-speed expansion ports 910, and a low speed interface 912 connecting to low speed bus 914 and storage device 906. Each of the components 902, 904, 906, 908, 910, and 912, are interconnected using various busses, and may be mounted on a common motherboard or in other manners as appropriate. The processor 902 can process instructions for execution within the computing device 900, including instructions stored in the memory 904 or on the storage device 906 to display graphical information for a GUI on an external input/output device, such as display 916 coupled to high speed interface 908. In other implementations, multiple processing units and/or multiple buses may be used, as appropriate, along with multiple memories and types of memory. Also, multiple computing devices 900 may be connected, with each device providing portions of the necessary operations (e.g., as a server bank, a group of blade servers, or a processing device).

The memory 904 stores information within the computing device 900. In one implementation, the memory 904 is a volatile memory unit or units. In another implementation, the memory 904 is a non-volatile memory unit or units. The memory 904 may also be another form of computer-readable medium, such as a magnetic or optical disk.

The storage device 906 is capable of providing mass storage for the computing device 900. In one implementation, the storage device 906 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 904, the storage device 906, or memory on processor 902.

The high speed controller 908 manages bandwidth-intensive operations for the computing device 900, while the low speed controller 912 manages lower bandwidth-intensive operations. Such allocation of functions is exemplary only. In one implementation, the high-speed controller 908 is coupled to memory 904, display 916 (e.g., through a graphics processor or accelerator), and to high-speed expansion ports 910, which may accept various expansion cards (not shown). In the implementation, low-speed controller 912 is coupled to storage device 906 and low-speed expansion port 914. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 900 may be implemented in a number of different forms, as shown in the figure. For example, it may be implemented as a standard server 920, or multiple times in a group of such servers. It may also be implemented as part of a rack server system 924. In addition, it may be implemented in a personal computer such as a laptop computer 922. Alternatively, components from computing device 900 may be combined with other components in a mobile device (not shown), such as device 950. Each of such devices may contain one or more of computing device 900, 950, and an entire system may be made up of multiple computing devices 900, 950 communicating with each other.

Computing device 950 includes a processor 952, memory 964, an input/output device such as a display 954, a communication interface 966, and a transceiver 968, among other components. The device 950 may also be provided with a storage device, such as a microdrive or other device, to provide additional storage. Each of the components 950, 952, 964, 954, 966, and 968, are interconnected using various buses, and several of the components may be mounted on a common motherboard or in other manners as appropriate.

The processor 952 can execute instructions within the computing device 950, including instructions stored in the memory 964. The processor may be implemented as a chipset of chips that include separate and multiple analog and digital processing units. The processor may provide, for example, for coordination of the other components of the device 950, such as control of user interfaces, applications run by device 950, and wireless communication by device 950.

Processor 952 may communicate with a user through control interface 958 and display interface 956 coupled to a display 954. The display 954 may be, for example, a TFT LCD (Thin-Film-Transistor Liquid Crystal Display) or an OLED (Organic Light Emitting Diode) display, or other appropriate display technology. The display interface 956 may comprise appropriate circuitry for driving the display 954 to present graphical and other information to a user. The control interface 958 may receive commands from a user and convert them for submission to the processor 952. In addition, an external interface 962 may be provided in communication with processor 952, so as to enable near area communication of device 950 with other devices. External interface 962 may provide, for example, for wired communication in some implementations, or for wireless communication in other implementations, and multiple interfaces may also be used.

The memory 964 stores information within the computing device 950. The memory 964 can be implemented as one or more of a computer-readable medium or media, a volatile memory unit or units, or a non-volatile memory unit or units. Expansion memory 984 may also be provided and connected to device 950 through expansion interface 982, which may include, for example, a SIMM (Single In Line Memory Module) card interface. Such expansion memory 984 may provide extra storage space for device 950, or may also store applications or other information for device 950. Specifically, expansion memory 984 may include instructions to carry out or supplement the processes described above, and may include secure information also. Thus, for example, expansion memory 984 may act as a security module for device 950, and may be programmed with instructions that permit secure use of device 950. In addition, secure applications may be provided via the SIMM cards, along with additional information, such as placing the identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 964, expansion memory 984, or memory on processor 952, that may be received, for example, over transceiver 968 or external interface 962.

Device 950 may communicate wirelessly through communication interface 966, which may include digital signal processing circuitry where necessary. Communication interface 966 may provide for communications under various modes or protocols, such as GSM voice calls, SMS, EMS, or MMS messaging, CDMA, TDMA, PDC, WCDMA, CDMA2000, or GPRS, EDGE, UMTS, LTE, among others. Such communication may occur, for example, through radio-frequency transceiver 968. In addition, short-range communication may occur, such as using a Bluetooth, WiFi, or other such transceiver (not shown). In addition, GPS (Global Positioning System) receiver module 980 may provide additional navigation- and location-related wireless data to device 950, which may be used as appropriate by applications running on device 950.

Device 950 may also communicate audibly using audio codec 960, which may receive spoken information from a user and convert it to usable digital information. Audio codec 960 may likewise generate audible sound for a user, such as through a speaker, e.g., in a handset of device 950. Such sound may include sound from voice telephone calls, may include recorded sound (e.g., voice messages, music files, etc.) and may also include sound generated by applications operating on device 950.

The computing device 950 may be implemented in a number of different forms, as shown in the figure. For example, it may be implemented as a cellular telephone 980. It may also be implemented as part of a smart phone 982, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing device that includes a backend component (e.g., as a data server), or that includes a middleware component (e.g., an application server), or that includes a front end component (e.g., a client computer having a graphical user interface or a Web browser through which a user can interact with an implementation of the systems and techniques described here), or any combination of such backend, middleware, or frontend components. The components of the system can be interconnected by any form or medium of digital data communication (e.g., a communication network). Examples of communication networks include a local area network ("LAN"), a wireless local area network ("WLAN"), a wide area network ("WAN"), and the Internet.

The computing device can include clients and servers. A client and server are generally remote from each other and typically interact through a communication network. The relationship of client and server arises by virtue of computer programs running on the respective computers and having a client-server relationship to each other.

A number of embodiments have been described. Nevertheless, it will be understood that various modifications may be made without departing from the spirit and scope of the embodiments described herein.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

What is claimed is:

1. A computer-implemented method for determining Ventricular Far Field contribution in atrial electrograms of a patient, the method comprising:
    receiving a plurality of electrical signals measured by a plurality of sensors wherein the plurality of electrical signals relate to a plurality of locations in an atrium of the patient;
    determining at least one reference signal measuring electrical excitation of the patient's ventricles;
    selecting from the plurality of the received electrical signals such electrical signals which are recorded under at least one of the following conditions:
        the respective signals are recorded at locations inside the atrium where the respective sensor has no contact to the atrial tissue,
        the respective signals are recorded, irrespective of the sensor location, during time intervals where the respective part of the atrium shows no electrical activity,
        the respective signals are recorded, irrespective of the sensor location, during time intervals which comprise a plurality of heart beat intervals and are subject to subsequent spatial smoothing; and
    determining a spatio-temporal distribution of the Ventricular Far Field inside the atrium by approximating the spatio-temporal distribution based on signal data of the selected signals by using an approximation model.

2. The method of claim 1, wherein the approximation model is selected from a linear spatial model, a non-linear spatial model, a temporal model, and a look-up table.

3. The method of claim 1, wherein approximating uses a polynomial approximation, approximation with a dipole source model, approximation with a spatio-temporal linear combination of the recorded signal data, approximation performed with Radial Basis Functions, approximation using Look-Up Tables, or an approximation performed by transforming the signal data to a regular grid before providing it in form of a Look-Up Table.

4. The method of claim 1, wherein the plurality of received signals comprises signal data recorded over multiple ventricular electrical excitation periods, the method further comprising:
    synchronizing the selected signal data with measured electrical excitation events, wherein determining the spatio-temporal distribution is based on the synchronized signal data.

5. The method of claim 4, wherein determining the spatio-temporal distribution of the Ventricular Far Field further comprises:
    generating a plurality of models wherein each model relates to a particular section within the atrium in combination with a particular time point in relation to at least one of the electrical excitation events and reflects a respective approximation of the Ventricular Far Field for the particular section at the particular time point.

6. The method of claim 1, further comprising:
    subtracting the contribution of the Ventricular Far Field at a location inside the atrium from the atrial electrogram represented by electrical signal data measured by a sensor at the location.

7. The method of claim 1, wherein determining the at least one reference signal further includes at least one of:
    receiving the at least one reference signal from one or more electrocardiogram sensors measuring at least the R wave of the patient's ventricular electrical activity,
    receiving the at least one reference signal from a coronary sinus catheter sensor, computing the at least one reference signal from the recorded electrical signal data by blind source separation or analysis of periodicity, or
    determining the at least one reference signal based on information about the ventricular contraction obtained by using laser interferometry, pulse oximetry, or near-infrared spectroscopy.

8. The method of claim 1, wherein the Ventricular Far Field contribution at the plurality of locations is extrapolated from the determined spatio-temporal distribution.

9. A computer program product for determining Ventricular Far Field contribution in atrial electrograms of a patient, the computer program product when loaded into a memory of a computing device and executed by at least one processor of the computing device executes instructions including:
    receiving a plurality of electrical signals measured by a plurality of sensors wherein the plurality of electrical signals relate to a plurality of locations in an atrium of the patient;
    determining at least one reference signal measuring electrical excitation of the patient's ventricles;
    selecting from the plurality of the received electrical signals such electrical signals which are recorded under at least one of the following conditions:
        the respective signals are recorded at locations inside the atrium where the respective sensor has no contact to the atrial tissue,
        the respective signals are recorded, irrespective of the sensor location, during time intervals where the respective part of the atrium shows no electrical activity,
        the respective signals are recorded, irrespective of the sensor location, during time intervals which comprise a plurality of heart beat intervals and are subject to subsequent spatial smoothing; and
    determining a spatio-temporal distribution of the Ventricular Far Field inside the atrium by approximating the spatio-temporal distribution based on signal data of the selected signals by using an approximation model.

10. The computer program product of claim 9, wherein approximating uses a polynomial approximation, approximation with a dipole source model, approximation with a spatiotemporal linear combination of the recorded signal data, approximation performed with Radial Basis Functions, approximation using Look-Up Tables, or an approximation performed by transforming the signal data to a regular grid before providing it in form of a Look-Up Table.

11. The computer program product of claim 9, wherein the plurality of received signals comprises signal data recorded over multiple ventricular electrical excitation periods, and the instructions further comprise:

synchronizing the selected signal data with measured electrical excitation events, wherein determining the spatio-temporal distribution is based on the synchronized signal data.

12. The computer program product of claim 11, wherein determining the spatio-temporal distribution of the Ventricular Far Field further comprises:

generating a plurality of models wherein each model relates to a particular section within the atrium in combination with a particular time point in relation to at least one of the electrical excitation events and reflects a respective approximation of the Ventricular Far Field for the particular section at the particular time point.

13. The computer program product of claim 9, wherein the instructions further comprise:

subtracting the contribution of the Ventricular Far Field at a location inside the atrium from the atrial electrogram represented by electrical signal data measured by a sensor at the location.

14. The computer program product of claim 9, wherein determining the at least one reference signal further includes at least one of:

receiving the at least one reference signal from one or more electrocardiogram sensors measuring at least the R wave of the patient's ventricular electrical activity, receiving the at least one reference signal from a coronary sinus catheter sensor, computing the at least one reference signal from the recorded electrical signal data by blind source separation or analysis of periodicity, or determining the at least one reference signal based on information about the ventricular contraction obtained by using laser interferometry, pulse oximetry, or near-infrared spectroscopy.

15. A computer system for determining Ventricular Far Field contribution in atrial electrograms of a patient, the computer system comprising:

an interface module configured to receive a plurality of electrical signals generated by a plurality of sensors wherein the plurality of electrical signals relate to a plurality of locations in an atrium of the patient;

a reference module configured to determine a reference signal reflecting electrical excitation of the patient's ventricles;

a data processing module configured to select from the plurality of the received electrical signals such electrical signals which are recorded under one or more of the following conditions:

the respective signals are recorded at locations inside the atrium where the respective sensor has no contact to the atrial tissue, the respective signals are recorded, irrespective of the sensor location, during time intervals where the respective part of the atrium shows no electrical activity, the respective signals are recorded, irrespective of the sensor location, during time intervals which comprise a plurality of heart beat intervals and are subject to subsequent spatial smoothing; and further configured to determine a spatio-temporal distribution of the Ventricular Far Field inside the atrium by approximating the spatio-temporal distribution based on signal data of the selected signals by using an approximation model.

16. The system of claim 15, wherein the approximation model is selected from a linear spatial model, a non-linear spatial model, a temporal model, and a look-up table.

17. The system of claim 15, wherein approximating uses a polynomial approximation, approximation with a dipole source model, approximation with a spatio-temporal linear combination of the recorded signal data, approximation performed with Radial Basis Functions, approximation using Look-Up Tables, or an approximation performed by transforming the signal data to a regular grid before providing it in form of a Look-Up Table.

18. The system of claim 15, wherein the plurality of received signals comprise signal data recorded over multiple ventricular electrical excitation periods, the data processing module further configured to:

synchronize the selected signal data with measured electrical excitation events, wherein determination of the spatio-temporal distribution of the Ventricular Far Field is based on the synchronized signal data.

19. The system of claim 18, wherein the data processing module includes a model generator to:

generate a plurality of models wherein each model relates to a particular section within the atrium in combination with a particular time point in relation to at least one of the electrical excitation events and reflects a respective approximation of the Ventricular Far Field for the particular section at the particular time point.

20. The system of claim 15, wherein the data processing module includes an atrial electrogram improvement module configured to:

subtract the contribution of the Ventricular Far Field at a particular location inside the atrium from the Atrial Electrogram represented by an electrical signal generated by one of the sensors at the particular location.

21. The system of claim 15, wherein the reference module is configured to determine at least one reference signal from at least one of the following list of potential reference signals:

the reference signal received from one or more electrocardiogram sensors measuring at least the R wave of the patient's ventricular electrical activity, the reference signal received from a coronary sinus catheter sensor, the reference signal computed from the recorded electrical signal data by blind source separation or analysis of periodicity, or the reference signal determined based on information about the ventricular contraction obtained by using laser interferometry, pulse oximetry or near-infrared spectroscopy.

* * * * *